United States Patent [19]

Wagner

[11] Patent Number: 5,394,094
[45] Date of Patent: Feb. 28, 1995

[54] PORTABLE GAS SENSOR UTILIZING FAULT PROTECTIVE BATTERY CAP

[75] Inventor: David D. Wagner, Sutersville, Pa.

[73] Assignee: Industrial Scientific Corporation, Oakdale, Pa.

[21] Appl. No.: 61,620

[22] Filed: May 13, 1993

[51] Int. Cl.$^6$ .......................... G01R 27/00; H02H 5/04
[52] U.S. Cl. .................................. 324/556; 340/632; 361/104; 439/621
[58] Field of Search .................. 324/555, 556, 133; 340/632, 664; 439/621, 622; 361/93, 104

[56] References Cited

U.S. PATENT DOCUMENTS

| | | | |
|---|---|---|---|
| 3,919,631 | 11/1975 | Brown | 324/133 |
| 4,134,112 | 1/1979 | Kercheval et al. | 340/632 |
| 4,255,698 | 3/1981 | Simon | 361/106 |
| 4,721,862 | 1/1988 | Cooper | 361/104 |
| 5,070,427 | 12/1991 | Bush | 361/104 |
| 5,136,452 | 8/1992 | Orton | 361/104 |
| 5,237,302 | 8/1993 | Harris | 361/104 |

FOREIGN PATENT DOCUMENTS

| | | | |
|---|---|---|---|
| 0074065 | 3/1991 | Japan | 439/621 |
| 404162691 | 6/1992 | Japan | 439/621 |

Primary Examiner—Maura K. Regan
Attorney, Agent, or Firm—Buchanan Ingersoll

[57] ABSTRACT

Portable gas sensing devices practicing the present invention include a fault protective battery cap to interrupt flow of battery current exceeding a preselected-threshold level. In normal operation, the battery cap is engaged with a compartment of the gas sensing device which maintains the battery used to power gas sensing circuitry therein. When installed in the gas sensing device in this manner, the battery cap defines a current path from at least one terminal of the battery to internal gas sensing circuitry. As with prior art battery caps, the battery cap of the invention is removable to facilitate replacement of the battery. Unlike prior art battery caps, however, battery caps constructed in accordance with the invention include a fuse electrically connected interposing the current path. The fuse functions to interrupt current flow from the battery if the current exceeds a preselected threshold level. In presently preferred embodiments, the battery cap is constructed of a generally nonconductive polymeric material which encapsulates a subminiature resistive fuse such that gas from the surrounding atmosphere is incapable of contacting the fuse.

11 Claims, 2 Drawing Sheets

PORTABLE GAS SENSOR UTILIZING FAULT PROTECTIVE BATTERY CAP

BACKGROUND OF THE INVENTION

1. Field of the Invention

The present invention relates to portable gas sensing devices of the type used to monitor atmospheric levels of selected gases in a combustible environment. More particularly, the invention relates to a portable gas sensor equipped with a fault protective battery cap to interrupt flow of battery current exceeding a preselected threshold level.

2. Description of the Prior Art

In many drilling, mining, and industrial situations, the atmosphere may occasionally contain gases which could prove hazardous to workers in the area. It is therefore often desirable in these situations that the workers carry a portable gas sensor for continually monitoring the atmospheric level of selected gases. If the concentration of the monitored gas rises above a desirable level, the worker will be alerted so that appropriate action can be taken. Preferably, these gas sensors are battery powered and small enough to be conveniently worn, for example, on the worker's belt.

Such portable gas sensors, as well as other instruments designed for use in locations where flammable or combustible material may be contained in the ambient atmosphere, should preferably meet a design standard referred to as "intrinsically safe." An instrument is referred to as "intrinsically safe" if it normally, or in specified fault conditions, will not produce a spark or other thermal action sufficient to cause ignition of the flammable or combustible material when mixed with air in its most easily ignitible concentration. Various agencies, such as Underwriters Laboratories, Factory Mutual Research, Canadian Standards Association and Cenelec, certify instruments as meeting or failing to meet this criteria.

Instruments having a design designated to be "intrinsically safe" generally incorporate current limiting elements to restrict current flow to levels which are considered acceptable in the event of certain internal faults. In portable instruments, fuses are commonly used to reduce the otherwise impracticable size and cost of other necessary current limiting elements such as resistors. A drawback in using a fuse, however, is that, in most cases, the fuse itself must be considered "intrinsically safe" such that any arc occurring from failure of the fuse element must be incapable of igniting a hazardous atmosphere. Therefore, the fuse generally must be encapsulated within a material that provides a gas tight seal about its body.

A common type of fuse utilized for this purpose is a commercially available "safety fuse" which resembles a large leaded resistor. In addition to being somewhat costly, this type of fuse is difficult to implement in a small portable instrument. "Intrinsically safe" fuses have also been constructed by encapsulating a fuse inside of a replaceable unit which also contains batteries used to power the instrument. This implementation has caused problems in that servicing of the instrument has typically resulted in failure of the fuse. As a result, replacement of the entire battery pack unit has often been necessitated even though the batteries frequently had remaining useful life.

SUMMARY OF THE INVENTION

Portable gas sensing or other electrical devices practicing the present invention include a fault protective battery cap to interrupt flow of battery current exceeding a preselected threshold level. Like prior art battery caps, the battery cap of the invention is engageable to maintain the battery within the device and removable to facilitate replacement of the battery. Unlike prior art battery caps, however, the invention includes a fuse which creates an open circuit if the battery current exceeds a preselected threshold level. In presently preferred embodiments, the battery cap is constructed of a generally nonconductive polymeric material encapsulating a subminiature resistive fuse. In this case, gas from the surrounding atmosphere is generally incapable of contacting the fuse, thereby meeting specified design requirements with greater economy and convenience than the prior art.

DETAILED DESCRIPTION OF PRESENTLY PREFERRED EMBODIMENT

In accordance with the invention, a fault protective battery cap may be provided for use in a portable gas sensor or other electrical device to interrupt flow of battery current exceeding a preselected threshold level. Under the teachings of the invention, as will be demonstrated, a number of distinct advantages are achievable when compared with the prior art. Particularly, the invention provides a means by which a fuse element, which would otherwise be installed along with other circuitry inside the housing of the gas sensor, may be more easily replaced should it fall during operation of maintenance. Furthermore, the requirements of an "intrinsically safe" designs may be met while simultaneously decreasing the size and space required by prior art current limiting components. Additionally, because the gas sensor cannot be operated (absent tampering) without the battery cap in position, the invention renders any attempt to bypass or substitute the fuse element very difficult.

Figure 1A:
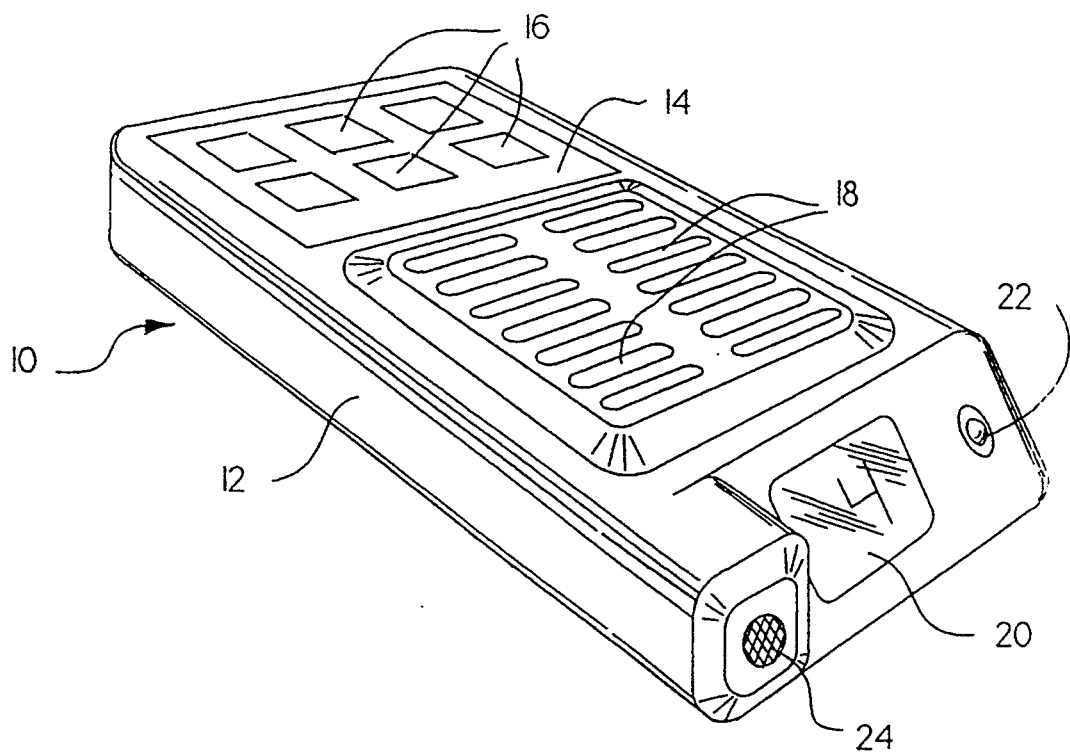
FIGS. 1A and 1B are opposite perspective views of a portable gas sensor constructed in accordance with the invention.
Figure 1B:
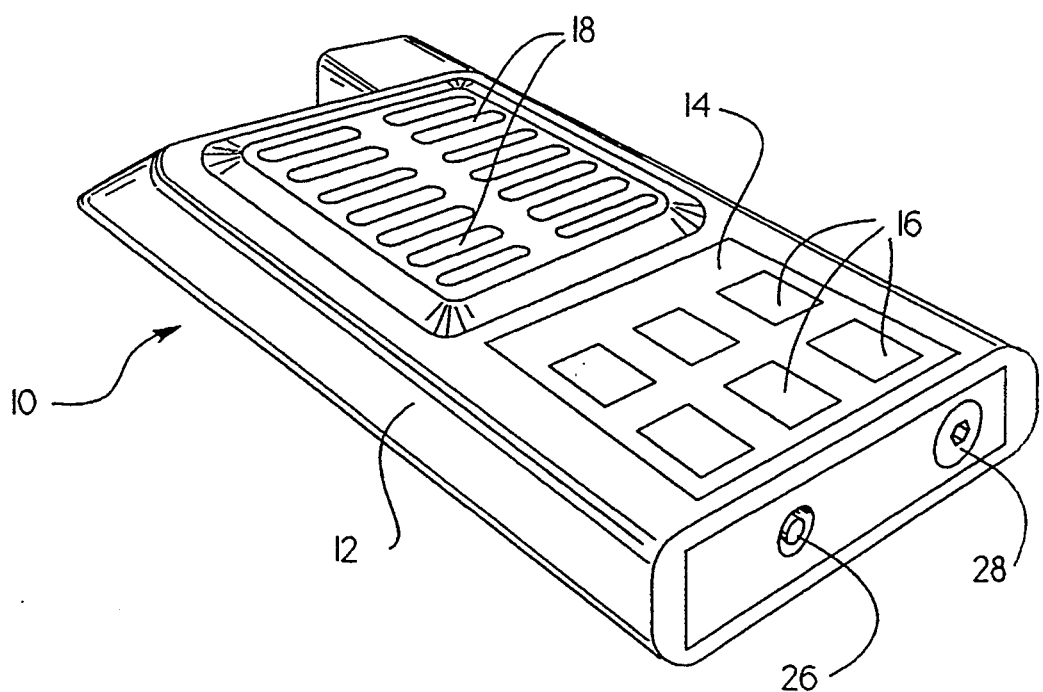

FIGS. 1A and 1B illustrate a portable gas sensor 10 constructed in accordance with the invention. Internal components of sensor 10 are enclosed within an outer housing 12. Housing 12 is preferably constructed of a conductive polycarbonate material to provide shielding to aberrant electromagnetic interferences. A Key pad panel 14 mounted on the top face of housing 12 includes a plurality of key pad switches 16 to facilitate control of gas monitoring functions by the user. A series of openings 18 also, located along the top face of housing 12 allow the monitored gas to diffuse into sensor 10 for analysis.

A number of indicators provide status information to the user concerning the concentration of the selected gas. For example, the concentration of the monitored gas is continually displayed on a digital readout 20. Additionally, a visual indicator, i.e., LED 22, illuminates to provide a visual indication that the concentration of the monitored gas has exceeded the threshold. Similarly, an audible indicator 24 provides an audible warning that the gas concentration has exceeded the desired threshold. A data port, such as RS-232 serial data port 26, may also be provided to transfer gas concentration data stored in sensor 10 during a period of exposure to an outboard computer or other analysis equipment.

Figure 2:
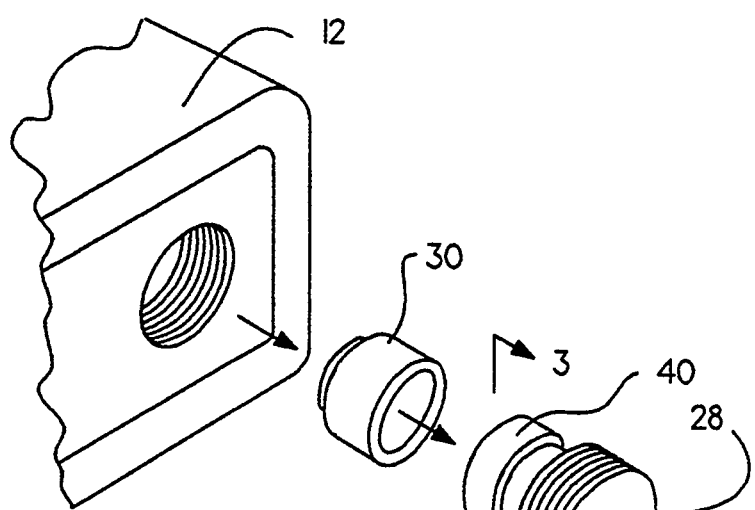
FIG. 2 is a fragmentary assembly view illustrating removal of the battery and battery cap from the gas sensor illustrated in FIGS. 1A and 1B.

Sensor 10 is powered by one or more replaceable batteries maintained within housing 12. In the normal situation in which battery cap 28 is engaged with housing 12, the battery is maintained within a battery compartment. As with many prior art battery caps, battery cap 28 includes conductors to provide a current path between at least one terminal of the battery and other circuitry within sensor 10. As is illustrated in FIG. 2, replacement of such a battery 30 is easily accomplished by removal of battery cap 28.

Figure 3:
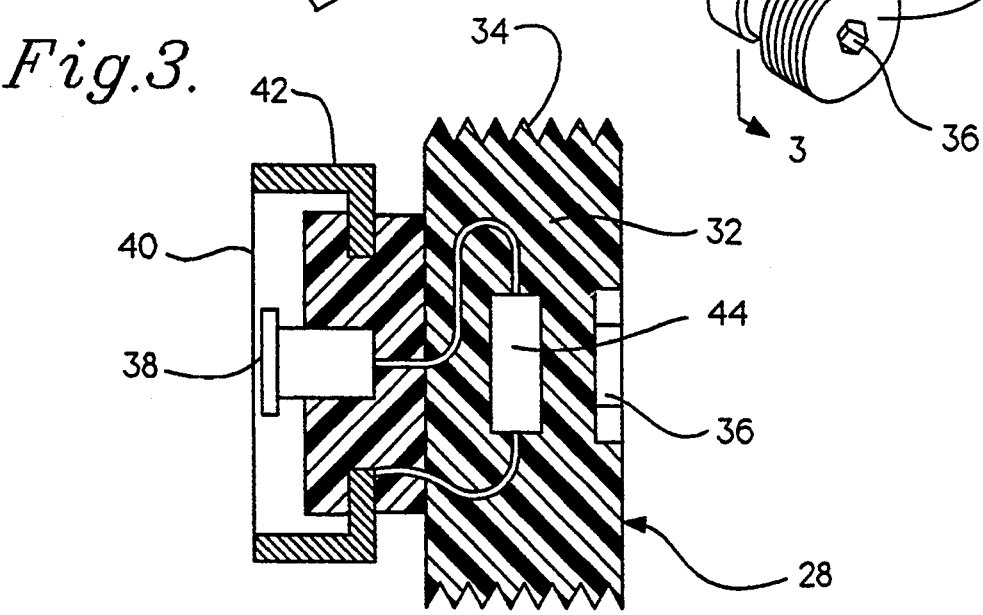
FIG. 3 is a partial cross-sectional view taken along line 3—3 of FIG. 2 illustrating a fault protective battery cap constructed in accordance with the invention.

The internal construction of battery cap 28 may be best understood with reference to FIG. 3. In presently preferred embodiments, battery cap 28 primarily comprises a molded battery cap body 32, which is preferably constructed of a nonconductive polymeric material. Body 32 is circumscribed by a series of threads 34 which are sized to matingly engage complementary threads within housing 12. While a simple coin slot or the like may be used to facilitate the unscrewing of battery cap 28, presently preferred embodiments utilize a hex opening 36 to discourage removal of the battery cap 30 by unauthorized personnel.

A metallic eyelet 38 is provided partially embedded within body 32 to contact the negative terminal of battery 30 when installed in housing 12. Eyelet 38 is electrically connected to a metallic ring 40 which defines an annular conducting surface 42. Conducting surface 42 contacts a conductive wiper (not shown) within housing 12 upon installation of battery cap 28 to complete the electrical circuit. It should be noted that, in order to facilitate passage of the metallic ring 40 sufficiently into housing 12, it should have a diameter slightly less than the opening within housing 12.

Unlike prior art battery caps, the present invention includes an interposing fuse element 44 within the current path between eyelet 38 and metallic ring 40. Fuse element 44 functions to interrupt current flow if the current passing between the negative terminal of battery 30 and other circuitry within gas sensor 10 exceeds a preselected threshold level. Preferably, fuse element 44 is a standard subminiature resistive fuse which is encapsulated within body 32. Because fuse element 44 is, in this instance, completely surrounded by nonconductive polymeric material, contact with combustible or flammable material in the ambient atmosphere is prevented. As a result, any arcing or other thermal action within fuse element 44 is generally incapable of igniting such flammable or combustible material. In this configuration, the fuse itself is not required to satisfy "intrinsically safe" design requirements in order for the device to meet these standards. Consequently, an economical standard fuse element may be utilized to reduce overall costs.

It can also be seen that the placement of fuse element 44 as an integral component within the battery cap 28 allows fuse replacement to be accomplished more easily than has been the case in the past. Additionally, this configuration insures that the fuse element will be removed from the gas sensing device prior to battery 30 when the instrument is serviced. As a result, a difficult-to-replace fuse element will not be caused to fail due to inadvertent short circuits or other current increases which may sometimes occur in the servicing process.

Figure 4:
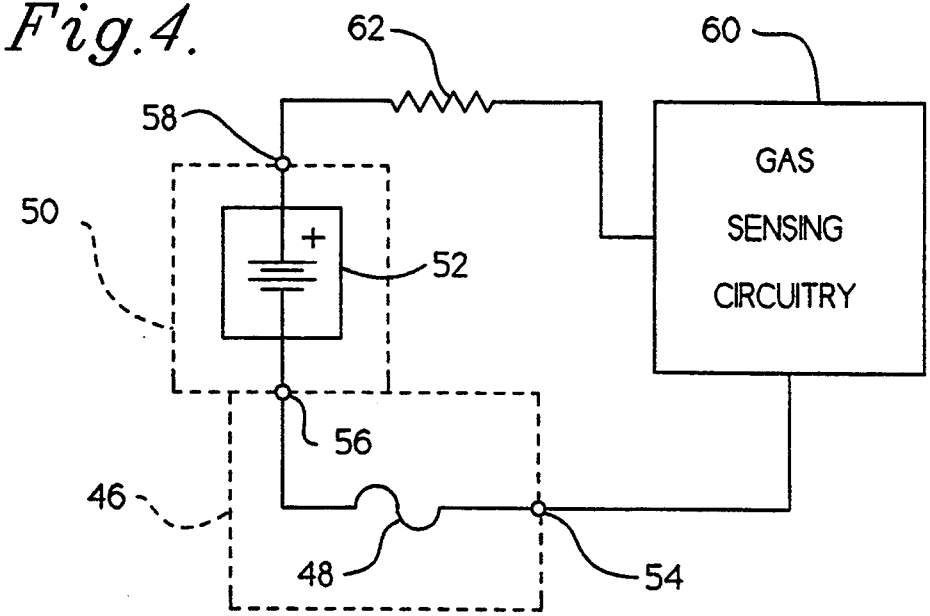
FIG. 4 is a schematic of the electrical connection of the fault protective battery cap of the invention in relation to the battery and other circuitry of the portable gas sensor.

FIG. 4 schematically illustrates electrical connection of the fuse element in relation to other components within device 10. Block 46, as shown in broken lines, is intended to represent battery cap 28. Fuse 48 within block 46 is representative of fuse element 44. Similarly, block 50, having therein a battery 52, represents the battery compartment within shell 12. A first connection point 54 is representative of the contact of metallic ring 40 with the conductive wiper within housing 12. A second connection point 56 illustrates electrical contact between eyelet 38 and the negative battery terminal. A third connection point 58 illustrates electrical connection between the positive battery terminal and a contacting conductor (not shown) within the internal battery compartment of shell 12. The overall gas sensing circuitry utilized to detect the selected gas is diagrammatically illustrated as block 60. A current limiting resistor 62, which may be made smaller than otherwise due to the presence of a serial fuse, is also provided. Gas sensing circuitry 60 and current limiting resistor 62 may be mounted on a single printed circuit board.

It can be seen that current will flow first from the positive terminal of battery 52 through connection point 58 and current limiting resistor 62 to gas sensing circuitry 60. A return path for the current is then provided through connection point 54, fuse 48, and connection point 56. Finally, the current completes the circuit by flowing back to the negative terminal of battery 52. It is thus evident that current exceeding a preselected threshold level as determined by the fuse 48 will be interrupted, thus preventing an undesirable fault condition of excessive current.

It can therefore be seen that the invention provides a fault protective battery cap for use with a portable gas sensing device to interrupt current flow exceeding a preselected threshold level. While certain presently preferred embodiments have been shown and described, it is to be distinctly understood that the invention is not limited thereto but may be variously embodied and practiced within the scope of the following claims.

I claim:

1. An improved portable gas sensing device of the type for monitoring atmospheric levels of selected gases in a combustible environment, the portable gas sensing device having electronic gas sensing circuitry powered by a battery contained within a battery compartment and maintained by a removable battery cap, the battery cap having current path means for contacting a terminal of the battery and establishing a current path for electrical current between the battery terminal and the electronic gas sensing circuitry, wherein the improvement comprises:

the removable battery cap containing a fuse electrically connected interposing said current path means for interrupting continuity of the current path if electrical current conducted through the current path exceeds a preselected level, the fuse being configured to prevent contact of gases in the combustible environment with the fuse.

2. The improved portable gas sensing device of claim 1 wherein the removable cap means is generally constructed of a nonconductive polymeric material, the fuse being encapsulated within the nonconductive polymeric material.

3. A battery assembly for use with a battery-powered portable electrical device, comprising:
   (a) compartment means for maintaining the battery within the portable electrical device;
   (b) removable cap means engageable with the compartment means for securing the battery, said removable cap means detachable from the compartment means to facilitate replacement of the battery;
   (c) current path means within the removable cap means for conducting electrical current from at least one terminal of the battery to circuitry within the portable electrical device when the removable cap means is in engagement with the portable electrical device; and
   (d) fuse means mounted within the removable cap means and electrically connected interposing a current path defined by the current path means for interrupting continuity of the current path mans if electrical current conducted through the current path exceeds a preselected level.

4. The battery assembly of claim 3 wherein the fuse means being mounted in the removable cap means in a manner that prevents gas from surrounding atmosphere from contacting the fuse means.

5. The battery assembly of claim 3 wherein the removable cap means is generally constructed of a nonconductive polymeric material, the fuse means being encapsulated within the nonconductive polymeric material.

6. The battery assembly of claim 3 wherein the fuse means comprises a subminiature resistive fuse.

7. A fault protective battery cap for use in a portable electrical device powered by at least one removable battery, the battery cap comprising:
   (a) a battery cap body constructed generally of a nonconductive polymeric material;
   (b) first conductor means for contacting a terminal of the battery when the battery and the battery cap are installed in the portable electrical device;
   (c) second conductor means for contacting a conductor of the portable electrical device when the battery cap is installed in the portable electrical device; and
   (d) fuse means electrically connected interposing the first conductor means and said second conductor means for interrupting flow of current from the battery if the current exceeds a preselected level, the fuse means further being encapsulated within said nonconductive polymeric material.

8. The battery cap of claim 7 wherein the battery cap body has a series of threads about an outer circumference thereof, the series of threads sized to matingly engage complementary threads in a housing of the portable electrical device.

9. The battery cap of claim 8 wherein the first conductor means comprises a metallic eyelet partially embedded in the battery cap body.

10. The battery cap of claim 9 wherein the second conductor comprises a metallic ring having an annular conducting surface circumscribing at least a portion of the battery cap body.

11. The battery cap of claim 10 wherein the fuse means comprises a subminiature resistive fuse.

* * * * *